United States Patent [19]
Baxter

[11] Patent Number: 5,866,597
[45] Date of Patent: Feb. 2, 1999

[54] USE OF TRIAZINE COMPOUNDS FOR THE TREATMENT OF MEMORY AND LEARNING DISORDERS

[75] Inventor: Martin George Baxter, Beckenham, United Kingdom

[73] Assignee: Glaxo Wellcome Inc., Research Triangle Park, N.C.

[21] Appl. No.: 900,868

[22] Filed: Jul. 25, 1997

Related U.S. Application Data

[63] Continuation of Ser. No. 535,140, Mar. 28, 1996, abandoned.

[30] Foreign Application Priority Data

Mar. 19, 1993 [GB] United Kingdom .................. 9305693

[51] Int. Cl.$^6$ .................................................. A61K 31/53
[52] U.S. Cl. .................................................................. 514/242
[58] Field of Search ...................... 514/383, 242

[56] References Cited

U.S. PATENT DOCUMENTS 5,629,312  5/1997  Bousseau et al. ...................... 514/242

FOREIGN PATENT DOCUMENTS

| | | |
|---|---|---|
| A-0 021 121 | 1/1981 | European Pat. Off. . |
| A-0 247 892 | 12/1987 | European Pat. Off. . |
| 0 519 602 | 12/1992 | European Pat. Off. . |
| A-0 519 602 | 12/1992 | European Pat. Off. . |

OTHER PUBLICATIONS

Drugs of the Future, J.R. Prous et al. (Eds.), vol. 11, No. 6, pp. 456–459, 1986.
Yuen et al., Epilepsia 33, Suppl. 3, pp. 82–83 (abstract only), 1992.
Epilepsia 27/5 (1986) 490–497.
Drugs of the Future, 11/6 (1986) 456–459.
Pico et al Developmental Brain Research, 9 (1983) 227–230 Brain glutamate inhibition and amnesia: evidence provided by proline analog action.
Sanger & Joly, 1991, Psychopharmacologoy, 104, 27–34 "Effects of NMDA receptor antagonists and sigma ligands on the acquisition of conditioned fear in mice".
Izquierdo, 1994, FASEB, 8, 1139–1145 "Pharmacological evidence for a role of long–term potentiation in memory".
Freed et al 1981, Pharmacology Biochemistry and Behavior, 14, 223–226 "Impairment of Instrumental Learning in Rats by glutamic Acid Diethyl Ester".
Provan et al 1992, Neurotoxicology, 13, 413–420 "Aluminum inhibits Glutamate Release from Transverse Rat Hippocampal Slices: Role of G Proteins, Calcium Channels and Protein Kinase C".

*Primary Examiner*—Raymond Henley, III
*Attorney, Agent, or Firm*—Nixon & Vanderhye

[57] ABSTRACT

The present invention is directed to the administration of 3,5-diamino-6-(2,3-dichlorophenyl)-1,2,4-triazine and its pharmaceutically and veterinarily acceptable acid addition salts for treating impaired memory and learning disorders.

6 Claims, No Drawings

USE OF TRIAZINE COMPOUNDS FOR THE TREATMENT OF MEMORY AND LEARNING DISORDERS

This is a rule 62 file wrapper continuation of application Ser. No. 08/535,140, filed Mar. 28, 1996, now abandoned.

The present invention relates to the use of 3,5-diamino-6-(2,3-dichlorophenyl)-1,2,4-triazine and its pharmaceutically and veterinarily acceptable acid addition salts in therapy.

EP-A-0 021 121 describes a group of triazines, including 3,5-diamino-6-(2,3-dichlorophenyl)-1,2,4-triazine, which are active in the treatment of disorders of the central nervous system, for example psychiatric and neurological disorders, and which are particularly useful as anticonvulsants, for instance in the treatment of epilepsy. These triazines are non-depressant and are therefore advantageous compared with depressant anti-epileptics such as phenobarbitone. EP-A-0 247 892 describes 3,5-diamino-6-(2,3-dichlorophenyl)-1,2,4-triazine isethionate, a particularly preferred salt owing to its good solubility.

In mechanistic studies, 3,5-diamino-6-(2,3-dichlorophenyl)-1,2,4-triazine has been shown to produce a use-dependent block of voltage-sensitive sodium channels (Lang et al, 1993, J. Pharm. Exp. Therap., 266, 829; Lees, G. and Leach, M. J., 1993, Brain Res., 612, 190) and at anticonvulsant brain concentrations to inhibit the release of excitatory amino acids, principally glutamate (Leach, M. J. et al, 1986, Epilepsia, 27, 490–497; Zhu, S. G. and McGee, E. G., 1990, Neurosci. Lett., 112, 348–351). Glutamate functions as an important neurotransmitter in the mammalian central nervous system and has also been identified as having specific actions in the peripheral nervous system. The known anticonvulsant effect of this compound has therefore been ascribed to its ability to act at voltage-sensitive sodium channels as an inhibitor of glutamate release.

Memory loss and impaired learning ability are features of a range of clinical conditions. For instance, loss of memory is the most common symptom of dementia states including Alzheimer's disease and senile dementia of the Alzheimer type (the two different terms here distinguish between young and old age onset cases). Alzheimer's disease is in fact the most important clinical entity responsible for progressive dementia in ageing populations. EP-A-0 275 668 reports that the 5HT$_3$-receptor antagonist ondansetron, 1,2,3,9-tetrahydro-9-methyl-3-[(2-methyl-1H-imidazol-1-yl)methyl]-4H-carbazol-4-one, has utility in the treatment of memory deficit and dementia states including senile dementia of the Alzheimer type.

Although the area of memory and learning impairment is rich in animal models which are able to demonstrate different features of memory and learning processes, there is currently no agreement as to which model provides the best predictive validity for clinical use (Hollister, L. E., 1990, Pharmacopsychiat., 23, (Suppl II) 33–36).

There is evidence that, in dementias, there is a marked loss of cholinergic neurones which mediate transmission to the neocortex and hippocampus. This loss is correlated with memory defects (Bartus et al, 1982, Science 217, 408–417). In animal experiments, cholinergic antagonists such as scopolamine given before or immediately after a learning trial can abolish the memory, as evidenced by lack of change in response on a second occasion (Spencer & Lal, 1983, Drug. Dev. Res., 3, 489–502). Reversal of the scopolamine effect has therefore been used to screen for nootropic compounds (also known as cognition enhancers). In this model cholinergic agonists and enhancers of cholinergic systems give positive results, as do piracetam and related compounds which do not interact with cholinergic systems in an obvious way (Pepeu & Spignoli 1989, Prog. Neuropsychopharmacol. Biol. Psychiat., 13, (Suppl) 577–588). A variety of other compounds have also given positive results, including vasoactive compounds, TRH and analogues, 5-HT$_3$ antagonists (e.g. ondansetron, referred to above), central stimulants, ACE inhibitors, opiate and dopamine antagonists, benzodiazepine receptor antagonists, ACTH analogues and alpha agonists.

The validation of any particular animal model is, however, hindered by the current lack of a standard nootropic drug for comparison. The few forms of treatment for memory loss and impaired learning available at present are not considered effective enough to make any significant difference to a patient (Hollister, L. E., ibid). There is therefore a need for new drugs which are clinically effective in treating memory defects and impaired learning.

It has now surprisingly been found that 3,5-diamino-6-(2,3-dichlorophenyl)-1,2,4-triazine and its salts can influence an essential part of the processes of memory and learning. Accordingly, the present invention provides the use, in the preparation of a medicament for the treatment of impaired memory or of a learning disorder, of 3,5-diamino-6-(2,3-dichlorophenyl)-1,2,4-triazine or a pharmaceutically or veterinarily acceptable acid addition salt thereof.

3,5-Diamino-6-(2,3-dichlorophenyl)-1,2,4-triazine will hereinafter be referred to as compound A. Compound A and its salts will be referred to collectively as the present compounds. The present compounds are non-toxic at prophylactically and therapeutically effective doses.

Suitable acid addition salts of compound A include those formed with both organic and inorganic acids. Such acid addition salts will normally be pharmaceutically and veterinarily acceptable. Examples of such salts include those formed with hydrochloric, sulphuric, citric, tartaric, phosphoric, lactic, pyruvic, acetic, succinic, fumaric, maleic, methanesulphonic, ethanesulphonic, oxaloacetic and isethionic acids. The salt with isethionic acid is preferred since it possesses particularly good solubility.

The present compounds may be prepared by a process which comprises cyclising the compound of formula (II):

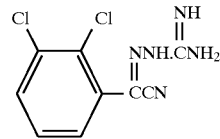

and, if desired, converting compound A thus obtained into a pharmaceutically or veterinarily acceptable acid addition salt.

The cyclisation is typically carried out by heating the compound of formula II under reflux in an alkanol, preferably a $C_{1-4}$ alkanol, for example methanol or ethanol, in the presence of a strong base, for example potassium hydroxide. The process may, for instance, be carried out as described in Example 1 of EP-A-0 021 121. The optional subsequent step of converting the compound A into an acid addition salt is performed by a conventional method, for example by treatment with the appropriate acid at ambient temperature. The salt with isethionic acid may be prepared, for instance, as described in EP-A-0 247 892, in particular in Example 3.

The starting compound of formula II may be prepared by the method described in U.S. Pat. No. 3,637,688.

Clinical conditions in which memory defects and impaired learning are prominent include, as mentioned above, Alzheimer's disease (AD) and senile dementia of the Alzheimer type (SDAT). AD refers to dementia with an onset prior to 65 years whereas SDAT refers to onset after 65 years. However, the neuropathological changes that are encountered in patients with AD and SDAT are virtually identical. There is a critical need for a drug to relieve the cognitive, especially memory, impairment that occurs in the early stages of AD and SDAT.

Memory defects also occur with other kinds of dementia such as multi-infarct dementia (MID), a senile dementia caused by cerebrovascular deficiency, and the Lewy-body variant of Alzheimer's disease with or without association with Parkinson's disease. Creutzfeld-Jakob disease is a rare dementia with which memory disorders are associated. It is a spongiform encephalopathy which is due to prion protein; it may be transmitted from other sufferers or may arise from gene mutations.

Loss of memory is a common feature of brain-damaged patients. Brain damage may occur, for example, after a classical stroke or as a result of an anaesthetic accident, head trauma, hypoglycaemia, carbon monoxide poisoning, lithium intoxication, vitamin (B1, thiamine and B12) deficiency, or excessive alcohol use.

Korsakow's disorder is a rare memory disorder which is characterised by profound memory loss and confabulation, whereby the patient invents stories to conceal his or her memory loss. It is frequently associated with excessive alcohol intake.

Memory impairment may furthermore be age-associated; the ability to recall information such as names, places and words seems to decrease with increasing age. Transient memory loss may also occur in patients, suffering from a major depressive disorder, after electro-convulsive therapy (ECT).

The available animal models of memory loss and impaired learning involve measuring the ability of animals to remember a discrete event. The passive avoidance procedure is the most widely used test. Here, the animal remembers the distinctive environment in which a mild electric shock is delivered and avoids it on a second occasion. However, this test has several disadvantages. A variant of the passive avoidance procedure therefore makes use of a rodent's preference for dark enclosed environments over light open ones, but shock is not used. Movement from a light box to a dark one has been used as a test for anxiolytic drugs in mice: Crawley, J. N., 1981, Pharmacol. Biochem. Behav., 15, 695–699; Costall, B. et al, 1987, Neuropharmacol., 26, 195–200; Costall, B. et al, 1989, Pharmacol. Biochem. Behav., 32, 777–785. The test is thought to capitalise on the conflict between exploratory drive and fear of unknown environments.

By measuring the latency to move from one compartment to the other, and testing on several occasions, the above-described test situation was modified to provide a test of learning and memory in mice: Barnes, J. M. et al, 1989, Br. J. Pharmacol., 98 (Suppl) 693P; Barnes, J. M. et al, 1990, Pharmacol. Biochem. Behav., 35, 955–962. In this test, the dark box is remembered on a second occasion as a "safe" place and there is less hesitation about entering.

The present compounds are active in the modified light-dark environment model described above, memory deficit having been induced in the tested animals by scopolamine. As reported in the Examples which follow, the effect of compound A on the scopolamine-induced memory deficit was determined in comparison with other compounds reported to be active in this or similar tests. The present invention therefore provides a method of treating impaired memory or a learning disorder in a mammal, the method comprising administering thereto a therapeutically effective amount of one of the present compounds. The present compounds can thus be used in the therapeutic treatment of clinical conditions in which memory defects or impaired learning occur. In this way memory and learning can be improved. The condition of a human being or animal can thereby be improved.

The present compounds have utility in treating clinical conditions and disorders in which impaired memory or a learning disorder occurs, either as a central feature or as an associated symptom. Examples of such conditions which the present compounds can be used to treat include Alzheimer's disease, senile dementia of the Alzheimer type, multi-infarct dementia and the Lewy-body variant of Alzheimer's disease with or without association with Parkinson's disease; Creutzfeld-Jakob disease and Korsakow's disorder.

The present compounds can also be used to treat impaired memory or learning which is age-associated, is consequent upon electro-convulsive therapy or which is the result of brain damage caused, for example, by stroke, an anaesthetic accident, head trauma, hypoglycaemia, carbon monoxide poisoning, lithium intoxication or a vitamin deficiency.

The present compounds are non-toxic at prophylactically and therapeutically effective doses. The orientative acute oral toxicity ($LD_{50}$) for compound A in mice is 250 mg/kg and in rats is 640 mg/kg. These are the dose levels at which 50% of the animals survive 10 days after administration of compound A.

The present compounds can be administered by a variety of routes and in a variety of dosage forms including those for oral, rectal, parenteral (such as subcutaneous, intramuscular and intravenous), epidural, intrathecal, intra-articular, topical and buccal administration.

The present compounds may be administered in any of the above dosage forms at a dose of from 1 mg/kg to 40 mg/kg per day, for example 5 mg/kg to 40 mg/kg, suitably 10 mg/kg to 30 mg/kg. For oral administration a dose of 40 mg/kg is particularly suitable. The dose range for adult human beings will depend on a number of factors including the age, weight and condition of the patient and the administration route. A typical dosage regimen is from 20 mg to 3200 mg per day, typically from 350 mg to 1400 mg per day, preferably from 600 mg to 1070 mg per day. It may in some situations be advantageous, since the present compounds are long-acting, to administer an initial dose of 70 mg to 3200 mg on the first day of treatment and then a lower dose of 20 mg to 1600 mg on subsequent days (all doses expressed as the base).

The present invention further provides a composition comprising a pharmaceutically or veterinarily acceptable carrier or diluent and, as an active principle, one of the present compounds. The composition can be prepared using conventional methods and administered in a pharmaceutically acceptable form.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavouring, preserving, suspending, thickening or emulsifying agents can be included.

When a suspension is prepared in water according to the present invention at least one of such agents will be present.

Other compounds which may be included by admixture are, for example, medically inert ingredients, e.g. solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolise to glucose or which metabolise only a very small amount to glucose. The suspensions and the emulsions may contain a carrier, for example a natural gum, agar, sodium alginate, pectin, methylcellulose, carboxymethylcellulose or polyvinyl alcohol.

Suspensions or solutions for intramuscular injection may contain, together with the active compound, a pharmaceutically acceptable carrier such as sterile water, olive oil, ethyl oleate, glycols such as propylene glycol and, if desired, a suitable amount of lidocaine hydrochloride. Solutions for intravenous injection or infusion may contain a carrier, for example, sterile water which is generally Water for Injection. Preferably, however, they may take the form of a sterile, aqueous, isotonic saline solution. Alternatively, the present compounds may be encapsulated within liposomes.

The present compounds may also be administered in pure form unassociated with other additives, in which case a capsule, sachet or tablet is the preferred dosage form.

Tablets and other forms of presentation provided in discrete units conveniently contain a daily dose, or an appropriate fraction thereof, of one of the present compounds. For example, units may contain from 5 mg to 500 mg, but more usually from 10 mg to 250 mg, of one of the present compounds (expressed as the base).

The invention is further illustrated in the Examples which follow.

EXAMPLE 1

Comparative Testing of Compound A in a Mouse Model of Memory Deficit

Methods and Materials (a) Animals & Dosing

Acute Dosing

Male albino CD-1 mice obtained from Charles River were used. They were housed under controlled conditions (temperature 21±2 deg. C., humidity approx. 50%, 12 hour light/dark cycle, food and water ad lib) for one week before use. On the day before test, the mice were housed in groups of six in polythene boxes in the laboratory and marked for identification. Food and water were supplied ad lib. On the test day, animals were weighed and then dosed either 30 minutes before test (piracetam, ondansetron) one hour before test (compound A) or immediately after test.

All drugs were dissolved or suspended in 0.25% (w/v) aqueous celacol, and administered orally (by gavage), i.p. or s.c. The dose volume was 10 ml/kg for all routes.

(b) Drugs

The following drugs were used. All doses are expressed as mg/kg base:

compound A ondansetron hydrochloride piracetam scopolamine hydrobromide (c) Apparatus The apparatus consisted of two boxes with an opening 90 mm×60 mm at floor level between them. A plastic door was used to close the opening when required. The smaller box (290 mm×120 mm×120 mm high) was made of opaque plastics, open at the top to allow illumination by normal laboratory lighting. The larger box (305 mm square×280 mm high) was enclosed apart from the single opening.

(d) Procedure

This consisted of training, with retest 24 hours later. During training, animals were placed individually in the open box facing away from the end with the opening. After a period of exploration, they usually entered the dark box and the latency to entry in seconds was noted. The door to the dark box was closed, and after 30 seconds had elapsed, the animal was removed gently and returned to the holding box. Twenty-four hours later, an identical procedure was used, except that the session ended as soon as the animal had entered the dark box. The latency was again noted. During the interval, the animals were not handled, and were disturbed as little as possible. Each animal was used once only.

Acute Dosing

Test drugs or control fluids were given before or immediately after the training session. Saline or scopolamine was administered 15 minutes before the training session. The dose of scopolamine, sufficient to prevent memory acquisition during the training session, was based on published work, i.e. 1 mg/kg in mice (Barzaghi, F. & Galliani, G., 1985, Br. J. Pharmacol, 86, 661P).

(e) Statistical Analysis

Group comparisons were made between latencies to enter the dark compartment on the first and second occasions. For both training and retest occasions, comparisons were made between vehicle and treatment groups. The distribution of latencies was skewed on both learning and retest trials (data not shown), so the non-parametric Mann-Whitney U-test was used. However, for convenience of illustration, group means±SEM are presented in the Tables. The difference between latencies on the two occasions is presented as % decrease on Day 2 compared with Day 1. Significance values between 0.06 and 0.1 are shown in brackets; * indicates that although the difference between latencies on the two test days was non-significant, there was a significant difference ($p<0.05$) between control and drug-treated groups on the same days.

The results are shown in the following Tables 1 and 2 and discussed below.

TABLE 1

Effect of compound A (A, p.o.), piracetam (Pirac, i.p.) or ondansetron (Ondan, i.p.) given pre-training as a single dose on scopolamine-induced deficit in mice

| Treatment on Day 1 | | Mean latency (secs) ± SEM | | Difference between days | |
|---|---|---|---|---|---|
| mg/kg s.c. | mg/kg p.o. or i.o. # | Day 1 | Day 2 | % Decrease | p |
| Saline | Celacol | 17.3 ± 1.7 | 9.9 ± 0.9 | 43 | <0.001 |
| Saline | A. 40 | 23.3 ± 3.4 | 12.8 ± 1.2 | 45 | <0.01 |
| Scop. 1 | Celacol | 18.8 ± 1.8 | 20.7 ± 2.3 | −10 | NS |
| Scop. 1 | A. 10 | 19.6 ± 1.7 | 17.1 ± 2.2 | 13 | NS |
| Scop. 1 | A. 20 | 18.6 ± 2.4 | 13.3 ± 1.5 | 28 | <0.05 |
| Scop. 1 | A. 40 | 22.1 ± 3.2 | 9.7 ± 1.2 | 56 | <0.001 |
| Saline | Saline | 18.9 ± 1.4 | 11.5 ± 0.8 | 39 | <0.001 |
| Saline | Pirac. 2000 | 21.4 ± 4.7 | 12.1 ± 1.2 | 44 | <0.01 |
| Scop. 1 | Saline | 18.9 ± 1.4 | 24.0 ± 2.5 | −27 | NS |
| Scop. 1 | Pirac. 2000 | 19.1 ± 2.4 | 13.9 ± 1.8 | 27 | NS* |
| Scop. 1 | Saline | 16.5 ± 1.3 | 16.8 ± 1.8 | −2 | NS |
| Scop. 1 | Ondan. 0.01 | 15.6 ± 1.8 | 20.0 ± 1.9 | −28 | NS |
| Scop. 1 | Ondan. 1.0 | 14.3 ± 1.4 | 14.9 ± 1.2 | −5 | NS |
| Scop. 1 | Ondan. 100 | 16.3 ± 1.9 | 11.8 ± 1.5 | 28 | <0.05 |

Ondansetron doses in ug/kg
*p < 0.05 compared with same day control

The mean latency to enter the dark box±standard error of the mean was calculated from a group of 12 animals. For a given treatment, figures in the columns labelled 'Day 1' and 'Day 2' show the mean latencies taken from the same group of animals. The difference between data obtained on the two days is illustrated by showing the % decrease, and the data compared using the Mann-Whitney U-test; NS indicates a p value>0.1.

Discussion of Table 1

Compound A: Mice treated with vehicle or with a single dose of compound A (40 mg/kg p.o.), in the absence of scopolamine one hour before training, showed the expected decrease in latency (43%, p<0.001 and 45%, p<0.01 respectively) on retest. Scopolamine (1 mg/kg) abolished this effect in vehicle-treated animals. Compound A at 10 mg/kg p.o. had no significant effect on the scopolamine-induced deficit (13% decrease in latency), whilst 20 mg/kg showed a significant reversal (28% decrease in latency, p<0.05) and 40 mg/kg abolished the deficit (56% decrease in latency, p<0.001).

Piracetam: Piracetam (2000 mg/kg i.p.) did not reverse the scopolamine-induced deficit as judged by the difference between Day 1 and Day 2 latencies (27% decrease, p>0.05). However, the Day 2 latency in the piracetam/scopolamine-treated animals was significantly different (p<0.05) from scopolamine-treated control animals run on the same day.

Ondansetron: Ondansetron (100 ug/kg, but not 1.0 or 0.1 ug/kg) given i.p. 30 minutes before training significantly reversed the scopolamine-induced deficit (28% decrease in latency, p<0.05). No vehicle/vehicle controls were used on this occasion.

TABLE 2

Effect of compound A (p.o. or i.v.) or piracetam (i.p.) given immediately post-training on scopolamine-induced deficit in mice

| Treatment on Day 1 | | Mean latency (secs) ± SEM | | Difference between days | |
|---|---|---|---|---|---|
| mg/kg s.c. | mg/kg | Day 1 | Day 2 | % Decrease | p |
| Saline | Comp. A.40 p.o. | 20.0 ± 2.3 | 13.9 ± 1.5 | 30 | <0.05 |
| Saline | Saline | 20.2 ± 3.0 | 14.2 ± 2.3 | 30 | <0.05 |
| Saline | Comp. A.20 i.v. | 19.9 ± 2.7 | 14.8 ± 2.1 | 26 | (0.09) |
| Saline | Piracetam 2000 i.p. | 18.8 ± 2.0 | 13.5 ± 1.7 | 28 | <0.05 |
| Scop. 1 | Saline | 19.5 ± 2.3 | 26.5 ± 2.7 | −36 | (0.07↑) |
| Scop. 1 | Comp. A.40 p.o. | 18.5 ± 1.8 | 22.7 ± 2.6 | −23 | NS |
| Scop. 1 | Comp. A.20 i.v. | 20.0 ± 2.3 | 20.3 ± 2.5 | −1 | NS |
| Scop. 1 | Piracetam 2000 i.p. | 19.2 ± 1.8 | 18.0 ± 1.8 | 6 | NS* |

*p < 0.05 compared with same day control
For legend see Table 1
Probability values in parantheses range from 0.05 to 0.1

For legend see Table 1
Probability values in parentheses range from 0.05 to 0.1

Discussion of Table 2

Table 2 shows the results of an experiment in which drugs were given immediately after removal of the mice from the dark box, in contrast to the results reported in Table 1 which were obtained with drug given before test. Compound A (40 mg/kg p.o. or 20 mg/kg i.v., the latter in an attempt to reduce the delay in onset of drug effects to a minimum) showed no reversal of the scopolamine-induced deficit. Piracetam (2000 mg/kg i.p.) did not reverse the scopolamine-induced deficit as judged by the difference between Day 1 and Day 2 latencies (6% decrease, p>0.05). However, the Day 2 latency in the piracetam/scopolamine-treated animals was significantly different (p<0.05) from scopolamine-treated control animals run on the same day.

EXAMPLE 2

Comparative Testing of Compound A in a Rat Model of Memory Deficit

Methods and Materials (a) Animals & Dosing

Acute Dosing

Male Wistar rats obtained from Charles River were used. They were housed under controlled conditions (temperature 21±2 deg. C., humidity approx. 50%, 12 hour light/dark cycle, food and water ad lib) for one week before use. On the day before test the rats were permanently housed in groups of six. Food and water were supplied ad lib. On the test day, animals were weighed and then dosed either 30 minutes before test (midazolam), one hour before test (compound A) or immediately after test.

Sub-acute Dosing

In the sub-acute dosing regimen (see 'Procedure') the rats, housed as above, received six doses of drug or vehicle by the oral route, each 24 hours apart.

All drugs were dissolved or suspended in 0.25% (w/v) aqueous celacol, and administered orally (by gavage), i.p. or s.c. The dose volume was 5 ml/kg for all routes.

(b) Drugs

The following drugs were used. All doses are expressed as mg/kg base:

compound A
midazolam hydrochloride scopolamine hydrobromide
(c) Apparatus

An identical apparatus to that described in Example 1 was used, except that the smaller box measured 370 mm×260 mm×190 mm.

(d) Procedure

This consisted of training as described for mice under section (d) of Example 1.

Acute Dosing

Test drugs or control fluids were given before or immediately after the training session. Saline or scopolamine was administered 15 minutes before the training session. The dose of scopolamine, sufficient to prevent memory acquisition during the training session, was based on in-house unpublished observations and was 0.1 mg/kg.

Sub-acute Dosing

The procedure was identical with that described above, except that seven groups of rats received compound A or control pre-treatment as 6 oral doses each 24 hours apart, as follows.

| Group | No. rats | Dose compound A mg/kg p.o. | | | | | |
|---|---|---|---|---|---|---|---|
| | | Day 1 | Day 2 | Day 3 | Day 4 | Day 5 | Day 6 |
| 1 | 24 | 0 | 0 | 0 | 0 | 0 | 0 |
| 2 | 12 | 0 | 0 | 0 | 0 | 10 | 0 |
| 3 | 12 | 0 | 0 | 0 | 0 | 40 | 0 |
| 4 | 12 | 0 | 0 | 0 | 0 | 10 | 10 |
| 5 | 12 | 0 | 0 | 0 | 0 | 40 | 40 |
| 6 | 12 | 2.5 | 2.5 | 2.5 | 2.5 | 2.5 | 2.5 |
| 7 | 12 | 10 | 10 | 10 | 10 | 10 | 10 |

Training took place 1 hour after the fifth dose i.e. on day 5. For each of the above treatment regimens, equal numbers of rats received saline or scopolamine 0.1 mg/kg 15 minutes before training, i.e. a total of 192 rats was used. The usual retest was performed 24 hours later (on day 6), one hour after the sixth oral treatment.

(e) Statistical Analysis

This was as described under section (e) of Example 1.

The results are shown in the following Tables 3 to 5 and discussed below.

TABLE 3

Effect of compound A given pre-training as a single oral dose on scopolamine-induced deficit in rats

| Treatment on Day 1 | | Mean latency (secs) ± SEM | | Difference between days | |
|---|---|---|---|---|---|
| mg/kg | | | | % | |
| s.c. | mg/kg | Day 1 | Day 2 | Decrease | p |
| Saline | Celacol | 33.4 ± 3.4 | 14.5 ± 2.8 | 56 | <0.001 |
| Saline | Comp. A.40 | 38.3 ± 3.8 | 19.3 ± 3.0 | 50 | <0.001 |
| Scop. 0.1 | Celacol | 44.4 ± 4.3 | 44.5 ± 3.7 | 0 | NS |
| Scop. 0.1 | Comp. A.10 | 40.8 ± 4.8 | 40.8 ± 4.6 | 0 | NS |
| Scop. 0.1 | Comp. A.20 | 37.7 ± 4.4 | 31.7 ± 3.9 | 16 | NS* |
| Scop. 0.1 | Comp. A.40 | 38.4 ± 4.1 | 21.1 ± 3.6 | 45 | <0.01 |

*p < 0.05 compared with same day control
For legend see Table 1 in Example 1

For legend see Table 1 in Example 1

Discussion of Table 3

Rats dosed p.o. with compound A or vehicle 1 hour before training showed a result very similar to that obtained with mice (Table 1 in Example 1). Rats dosed with vehicle showed the expected decrease in latency on retest (56%, p<0.001). Scopolamine reversed this effect. Compound A (40 mg/kg) reversed the scopolamine-induced deficit (45% decrease in latency, p<0.01).

An anxiolytic effect, by allowing the rats to stay longer in the light box on the first occasion, could present as a false positive on the part of the test compound. Midazolam, a typical benzodiazepine anxiolytic, was therefore tested to examine this possibility.

TABLE 4

Effect of midazolain given pre-training as a single i.p. dose on scopolamine-induced deficit in rats

| Treatment on Day 1 | | Mean latency (secs) ± SEM | | Difference between days % | |
|---|---|---|---|---|---|
| s.c. | mg/kg i.p. | Day 1 | Day 2 | Decrease | p |
| Saline | Saline | 31.3 ± 4.3 | 15.5 ± 2.3 | 50 | <0.01 |
| Saline | Midazol 0.5 | 39.9 ± 4.9 | 28.2 ± 2.7 | 29 | (0.09) |
| Scop. 0.1 | Saline | 34.4 ± 5.2 | 39.8 ± 4.5 | −16 | NS |
| Scoo. 0.1 | Midazol 0.5 | 37.0 ± 4.0 | 33.6 ± 3.4 | 9 | NS |

For legend see Table 1 in Example 1

Probability values in parentheses range from 0.05 to 0.1

Discussion of Table 4

Vehicle-treated rats showed the expected decrease in mean latency on retest (50% decrease in latency, p<0.01). Scopolamine prevented this effect. In the presence of midazolam alone (0.5 mg/kg i.p.), a reduction in latency was seen on retest (29% decrease in latency) which did not reach significance (p=0.09). This dose of midazolam did not reverse the scopolamine-induced deficit, indicating that any anxiolytic action is insufficient to account for the results obtained in this model with compound A.

TABLE 5

Effect of compound A given a) pre-training, b) pretraining and pre-retest or c) as four pre-treatments and before both training and retest

| s.c. Day 5 | Oral treatments mg/kg | | | Mean lat (secs) ± SEM | | Diff. between days | |
|---|---|---|---|---|---|---|---|
| mg/kg | Days 1–4 | Day 5 | Day 6 | Day 5 | Day 6 | % | p |
| Saline | Celacol | Celacol | Celacol | 34.5 ± 2.6 | 17.4 ± 1.7 | 50 | <0.001 |
| Scop. 0.1 | Celacol | Celacol | Celacol | 33.5 ± 2.2 | 34.4 ± 2.5 | −3 | NS |
| Saline | Cclacol | Comp. A.10 | Celacol | 39.8 ± 3.9 | 19.3 ± 2.5 | 52 | <0.001 |
| Saline | Celacol | Comp. A.40 | Celacol | 35.2 ± 3.4 | 19.3 ± 3.4 | 45 | <0.01 |
| Scop. 0.1 | Celacol | Comp. A.10 | Celacol | 34.3 ± 2.8 | 15.8 ± 4.5 | −4 | NS |
| Scop. 0.1 | Celacol | Comp. A.40 | Celacol | 33.3 ± 2.6 | 18.0 ± 2.0 | 46 | #0.001 |
| Saline | Celacol | Comp. A.10 | Comp. A.10 | 37.2 ± 3.1 | 19.3 ± 2.6 | 48 | <0.001 |
| Saline | Celacol | Comp. A.40 | Comp. A.40 | 36.0 ± 3.2 | 17.8 ± 2.2 | 50 | <0.001 |
| Scop. 0.1 | Celacol | Comp. A.10 | Comp. A.10 | 38.2 ± 4.3 | 27.7 ± 3.5 | 28 | NS (0.1) |
| Scop. 0.1 | Celacol | Comp. A.40 | Comp. A.40 | 33.6 ± 3.6 | 17.5 ± 2.5 | 48 | <0.01 |
| Saline | Comp. A.2.5 | Comp. A.2.5 | Comp. A.2.5 | 35.3 ± 3.7 | 19.3 ± 2.5 | 46 | <0.01 |
| Saline | Comp. A.10 | Comp. A.10 | Comp. A.10 | 34.3 ± 3.6 | 19.1 ± 3.4 | 44 | <0.01 |
| Scop. 0.1 | Comp. A.2.5 | Comp. A.2.5 | Comp. A.2.5 | 33.8 ± 3.0 | 28.4 ± 3.4 | 16 | NS |
| Scop. 0.1 | Comp. A.10 | Comp. A.10 | Comp. A.10 | 35.4 ± 3.2 | 20.8 ± 3.6 | 41 | <0.01 |

The mean latency to enter the dark box±standard error of the mean was calculated from a group of 24 animals (controls in first block) or 12 animals (all other treatments). For a given treatment, figures in the columns labelled 'Day 5' and 'Day 6' show the mean latencies taken from the same group of animals. The difference between data obtained on the two days is illustrated by showing the % decrease, and the data compared using the Mann-Whitney U-test.

NS indicates a p value>0.1

Discussion of Table 5

Vehicle-treated rats showed the expected decrease in mean latency (50%, p<0.001), which was reversed by scopolamine. Table 5 (second block) shows that a single dose of compound A of 10 mg/kg given before the learning trial did not alter the scopolamine-induced deficit. However, 40 mg/kg compound A produced a complete and highly significant reversal (46% decrease in mean latency; p<0.001). This result effectively replicates results described above but with additional doses of vehicle.

Table 5 (third block) shows that when a second dose of compound A was given before the retest, 10 mg/kg showed a trend to reversal of the scopolamine-induced deficit (28% decrease in mean latency; p=0.1), not seen after the single dose, and 40 mg/kg was maximally effective (48% decrease in mean latency; p<0.01).

Table 5 (fourth block) shows the effect of four further pretreatments with compound A, 2.5 or 10 mg/kg daily (i e. six doses in total). No significant effects were seen in the group treated with 2.5 mg/kg daily (16% reduction in latency). In contrast, 10 mg/kg daily produced a highly significant and maximal reversal of the scopolamine-induced deficit (i.e. 41% decrease in mean latency; p<0.01), similar to that produced by a single dose of 40 mg/kg.

EXAMPLE 3

Testing of Compound A in a Salivation and Pupil Measurement Test in Rats

Male Wistar rats (as used in Example 2) were dosed once only with compound A (10 or 40 mg/kg p.o.) or celacol control, one hour before observation and with scopolamine hydrobromide (0.1 mg/g s.c., calculated as the base) or saline control. 15 minutes before observation. Under these conditions, which were identical to those used in the learning experiments described in Example 2, changes in salivation and pupil diameter were measured. Salivation was measured by placing a piece of folded filter paper in the rat's mouth and measuring the diameter of the blot in mm after 1 minute. Pupil diameter was measured using a magnifying glass and graticule under normal lighting conditions. For both measures, comparisons were made between control and drug-treated groups using a Student's T-test on independent samples.

The results are shown in Table 6 below. Groups of 6 animals were used.

TABLE 6

Lack of effect of compound A on scopolamine-induced dry mouth and pupillary dilatation in rats

| Treatment mg/kg p.o. | Treatment mg/kg s.c. | Mean pupil diameter (mm × 10) ± SEM | Mean salivation (blot diameter mm) ± SEM |
|---|---|---|---|
| Celacol | Saline | 6.29 ± 0.47 | 8.79 ±0.38 |
| Compound A 10 | Saline | 7.00 ± 0.58 | 8.75 ± 1.11 |
| Compound A 40 | Saline | 7.75 ± 0.85 | 8.25 ± 0.63 |
| Celacol | Scopolamine 0.1 | 22.8 ± 1.65 | 2.88 ± 0.38 |
| Compound A 40 | Scopolamine 0.1 | 23.0 ± 1.78 | 2.13 ± 0.63 |

Discussion of Table 6

In vehicle-pretreated rats, scopolamine significantly increased pupil diameter and reduced salivation (p<0.01 all comparisons). Compound A pretreatment had no influence on the scopolamine-induced changes (all comparisons between vehicle and compound A-treated groups p>0.05).

EXAMPLE 4

Pharmaceutical Compositions

Tablets for oral administration are formulated with the following ingredients:

| | |
|---|---|
| Compound A | 150 mg |
| Lactose | 200 mg |
| Maize starch | 50 mg |
| Polyvinylpyrrolidone | 4 mg |
| Magnesium stearate | 4 mg |

Mix the active compound with the lactose and starch and granulate with a solution of the polyvinylpyrrolidone in water. Dry the resulting granules, mix with the magnesium stearate and compress to give tablets of average weight 408 mg.

I claim:

1. A method of treating impaired memory or a learning disorder in a mammal, the method comprising administering thereto a therapeutically effective amount of a compound selected from 3,5-diamino-6-(2,3-dichlorophenyl)-1,2,4-triazine and the pharmaceutically and veterinarily acceptable acid addition salts thereof.

2. The method according to claim 1 wherein the mammal is man.

3. A method according to claim 1, wherein the pharmaceutically acceptable salt is formed with isethionic acid.

4. A method according to claim 1, which comprises administration of 5 mg/Kg to 40 mg/Kg of 3,5-diamino-6-(2,3-dichlorophenyl)-1,2,4-triazine.

5. A method according to claim 1, which comprises oral administration of 40 mg/Kg of 3,5-diamino-6-(2,3-dichlorophenyl)-1,2,4-triazine.

6. A method according to claim 1, which comprises administration of a composition formulated with the following ingredients

| | |
|---|---|
| 3,5-diamino-6-(2,3-dichlorophenyl)-1,2,4-triazine | 150 mg |
| lactose | 200 mg |
| maize starch | 50 mg |
| polyvinylpyrrolidone | 4 mg |
| magnesium stearate | 4 mg |

* * * * *